United States Patent [19]

Morgan

[11] Patent Number: 5,407,953
[45] Date of Patent: Apr. 18, 1995

[54] TREATING APNEA/HYPOPNEA/SNORING IN HUMANS

[76] Inventor: Julia A. Morgan, 8398 Harvest St., Richland, Mich. 49083

[21] Appl. No.: 191,786

[22] Filed: Feb. 4, 1994

[51] Int. Cl.⁶ ............................................ A61K 31/415
[52] U.S. Cl. ..................................................... 514/397
[58] Field of Search ........................................ 514/397

[56] References Cited

PUBLICATIONS

Ehmbace abstract of Chessen et al. Dis. Nerv. Syst. 35(4): 152-153 (1974) "ECT, Glaucoma, and Prolonged Apnea".
D. H. Chessen, et al, Diseases of the Nervous System, vol. 35, No.4, Apr., 1974, pp. 152-152, "ECT . . . Prolonged Apnea".
Goldstein, A., et al, Princ. of Drug Action, 2nd Ed., 1968 pp. 140-141, (re fatal apnea).
C&E NEWS, Sep. 6, 1971, pp. 20, 22; (re ALZA, Ocusert TM).
Weinstein Modern Medicine, Oct.30–Nov. 15, 1978, pp. 26-33. (re sleep disorders.
Lange's BASIC . . . Pharmacology, 3rd Edit., 1987, pp. 64-68. (re cholinoceptor stimulants).
PDR, 17th Edit., 1989, for Opthalmology, p. 105. (re ALZA's OCUSERT TM pilocarpine).
Korolkovas, A., Essentials of Med. Chem., 2nd Edit., 1988, pp. 114-117 (re pilocarpine esters).
Young et al., The New England J. of Medicine, Apr. 29, 1993, pp. 1230-1235, (re sleep disorders).
PDR (for Opthalmology), 1993, p. 3, (re MIOTICS including pilocarpine salts).
Medline Express TM computer search report, 6 pp., re terms "Apnea", Sleep Apnea syndromes done in 1993-1994.

*Primary Examiner*—Shep K. Rose
*Attorney, Agent, or Firm*—John T. Reynolds

[57] ABSTRACT

This invention provides a method for treating sleep apnea, hypopnea and/or snoring in a human patient by administering to said patient a compound that results in the release of pilocarpine to the nasopharnyx and hypopharnyx tissues an amount effective to reduce or eliminate such sleep apnea, hypopnea and snoring condition in such patient.

Pilocarpine hydrochloride and pilocarpine nitrate in sustained release ocular compositions are preferred for convenience but other forms such as eye-drop solutions or aqueous gel forms may also be used. Pro-drug or targeted drug forms of pilocarpine that result in more effective tissue absorption and subsequent release of the pharmacologically active pilocarpine may also be utilized.

11 Claims, No Drawings

TREATING APNEA/HYPOPNEA/SNORING IN HUMANS

FIELD OF THE INVENTION

This invention relates to a method for treating apnea, hypopnea and snoring in human patients suffering from such conditions. More particularly, this invention provides a new medical use of known pilocarpine compounds for treating apnea, hypopnea and snoring in a human patient by administering a compound that results in a therapeutic amount of pilocarpine being released to relieve those apnea, hypopnea and snoring conditions in such patient.

BACKGROUND OF THE INVENTION

Recent studies have shown that approximately two percent of women and four percent of men in the middle-class workforce have sleep apnea syndrome (T. Young, et al, *The New England Journal of Medicine*, pp. 1230, Apr. 29, 1993). The current treatment for this condition requires the use of an unwieldy positive air-pressure appliance during sleep, for the rest of the patients life. No other effective treatments have yet been devised that would alleviate these sleep-disorders.

Other publications report on research studying the effects of other drugs on sleep apnea. *The J. of Psychosom. Research.*, 1993, 37 Suppl. 1;pp 59–65, reports studies on the use of benzodiazepine hypnotic type compounds for patients with obstructive sleep apnea syndrome. However, benzodiazepine hypnotic drugs are quite potent and are not preferred by some doctors and patients because of some alleged side-effects.

*The Am. Rev. Respir. Dis.*, 1992, June, Vol. 145 (6), pp 1378–83 reports on studies of gamma-hydroxybutyrate in patients with obstructive sleep apnea. No significant improvement over a control group was seen in this study.

*The Am. Rev. Respir. Dis*, 1992, February, Vol 145 (2 Pt 1): pp 435–9 reports on the effect of clonidine hydrochloride on obstructive sleep apnea in male patients. It was reported that clonidine had no effect on the frequency and duration of non-REM breathing abnormalities.

Other publications reporting on the effect of other medicinal agents on sleep-related snoring or sleep apnea disorders include:

a) *Drugs*, 1991; 41 Supp 1: pp 37–47 (cilazapril);

b) *Chest,* 1991; August, Vol. 100 (2): pp 416–421 (protriptyline), which is used to treat obstructive sleep apnea, but has anticholinergic side-effects;

c) *Am. Res. Respir. Dis.,* 1991; Nov, Vol 144 (5): pp 1112–1120, reports on studies of the basic mechanism of sleep-disordered breathing during rapid-eye-movement (REM) in the English bulldog.

d) *Lancet,* 1991, July 27; 338 (8761); pp 251–252, (oestradiol and medroxyprogesterone)

e) *J. Clin. Psychopharmacol.*, 1991, February, Vol. 11,(1); pp 71–72. (Buspirone)

f) *Lung*, 1990; Vol. 168 Supp, pp 948–954 (Almitrine).

None of the above drug treatments are believed to be as effective in treating snoring, sleep apnea and hypopnea in humans as what has been discovered according to this invention.

It is an object of this invention to provide a treatment method for reducing and preferably eliminating the snoring and/or sleep apnea and hypopnea events in human patients suffering from such conditions with a class of drug compounds which are used for other ailments, which are safe and relatively easy to administer to the patient.

SUMMARY OF THE INVENTION

This invention provides a method for treating apnea, hypopnea and snoring in a human patient suffering from such conditions which entails administering to the patient a compound that releases or will release pilocarpine in an amount effective to reduce such apnea, hypopnea and snoring conditions in such patient. The preferred pilocarpine compounds are salts such as pilocarpine hydrochloride and pilocarpine nitrate. The selected pilocarpine compounds are preferably administered in a shaped or gel pharmaceutical unit which will deliver to the patient from about 20 to 40 micrograms per hour, when administered via the eye cul-de-sac route or to an other conjunctive surface in continuous release form over an extended time period such as a seven day period. Specific therapeutic amounts of pilocarpine may vary depending upon route of administration, the selected pilocarpine compound or composition, and the particular physical size and physiological character of patient. However the pilocarpine is effective to treat the patient as soon as it is placed in contact with any conjunctive surfaces from which the drug penetrates into peripheral tissues. Commercially available ophthalmic medication forms of pilocarpine salts are available for use according to this invention.

DETAILED DESCRIPTION OF THE INVENTION

Pilocarpine is known by a variety of proprietary names including Adsorbocarpine, Akarpine, Isopto Carpine, Pilocar, Pilocel, Pilopine HS, P.V. Carpine and the like. The chemical name of pilocarpine is 3-ethyldihydro-4[(1-methyl-1H-imdazol-5-yl)methyl]-2(3H)-furanone. Pilocarpine is extracted from the dried leaflets of *Pilocarpus jaborandi* or *P. microphyllus*, where it occurs to the extent of approximately 0.5 percent. Pilocarpine occurs as a viscous, hygroscopic, colorless, oily liquid, or crystals. It is soluble in water, alcohol and chloroform; it is sparingly soluble in ethyl ether, and practically insoluble in light pretoleum. Pilocarpine hydrochloride occurs as colorless, odorless translucent, faintly bitter crystals. It is very soluble in water, freely soluble in alcohol, slightly soluble in chloroform and insoluble in ethyl ether. Pilocarpine nitrate (P.V. Carpine) occurs as shining, white crystals; it is stable in air, being affected by light. It is freely soluble in water, sparingly soluble in alcohol, and insoluble in chloroform and ethyl ether. A commercially obtainable sustained release form of pilocarpine is sold under the OCUSERT trade name, as OCUSERT ® Pilo-20 brand of pilocarpine as an ocular therapeutic system which administers about 20 micrograms per hour for one week and Ocusert ® Pilo-40 brand of pilocarpine as an ocular therapeutic system which releases about 40 micrograms of pilocarpine per hour for one week. This form consists of two outer alginic acid based membranes with a central reservoir of pilocarpine. Another long acting preparative is pilocarpine gel (Pilopine HS gel); it contains pilocarpine in an aqueous gel form. Aqueous solutions of pilocarpine salts, principally the chloride or nitrate, can also be used.

Pilocarpine is classified as a direct-acting cholinomimitic alkaloid. It preferentially binds and activates the muscarinic receptors, producing a parasymathetic effect to smooth muscle *Basic and Clinical Pharmacology*, Katzung, B. G., 3rd Ed., Appleton and Lange, Norwalk, Conn., pp 63–74). It is known that pilocarpine can induce an asthmatic attack and even induce fatal apnea through its stimulatory effect on the bronchiolar smooth muscle and the tracheobronchial mucosa, if drug exposure occurs, in aerosol form (*Principals of Drug Action*, A. Goldstein et al, 2nd Ed., John Wiley & Sons, New York, N.Y.). Therefore, the use of an asthma/apnea-inducing agent, such as pilocarpine, for the treatment of apnea is believed to be unexpected.

If pilocarpine is administered by a pharmacokinetically selective route, e.g., through a conjunctival surface, the parasympathetic effects are localized to the surrounding tissues, systemic drug levels are minimal, and thus the untoward side-effects are significantly reduced, in comparison to other routes of drug administration, such as oral bolus or parental injection.

The localized therapeutic response of contraction of the smooth muscle of the iris sphincter and of the ciliary muscle results in the safe and common utility of pilocarpine for the treatment of the symptoms of glaucoma. Likewise, we believe that the stimulatory effect of pilocarpine upon the localized smooth muscles of the nasopharnyx and hypopharnyx results in an alleviation of the nasophyrangeal obstruction that is the apparent cause of obstructive sleep apnea (*Modern Medicine*, Oct. 30, 1978, pp 26–33.) and snoring. The localized administration of pilocarpine for the treatment of recurrent neonatal apnea, may also prove to be beneficial. The effect of pilocarpine on the mechanism of central apnea, where diaphragmatic motion is interrupted, is not known.

Applied topically, pilocarpine is used as a miotic of choice in the treatment of primary open-angle glaucoma, in many chronic glaucomas and in the emergency treatment of acute angle-closure glaucoma. Pilocarpine is also used to antagonize the effect of short-acting mydriatics of the eye.

Pilocarpine can be administered in dosage forms similar or identical to those currently used for its miotic action. One or more drops of one or two percent, in the form of a pilocarpine salt solution, instilled in the conjunctival sac, repeated every four to eight hours, if necessary; sometime concentrations of four percent pilocarpine salt aqueous solutions are recommended. A preferred method of dosage for some people is to place a sustained release form of the pilocarpine compound, e.g., pilocarpine hydrochloride or pilocarpine nitrate, in the upper or lower ocular cul-de-sac at bedtime, such as the above mentioned OCUSERT ® sustained release form, which form should be replaced every seven days. Pilocarpine gel can be applied topically to the lower conjunctival cul-de-sac at bedtime. Bioprecursors of pilocarpine, such as the monoesters and the more lipophilic diesters of pilocarpine, synthesized by Bundgaard and reported in *Essentials of Medicinal Chemistry*, A. Korolkovas, 2nd Ed., John Wiley & Sons, 1988, may also be utilized, pp. 114–116.

EXAMPLE

This invention was discovered when a family member observed over time that a spouse, who was being treated for a glaucomatous condition with a topical miotic agent, experienced total cessation of chronic sleep apnea and snoring while on the pilocarpine-based medication. A disturbed sleep pattern of loud snoring, interrupted by frequent 20–30 second intervals of apnea, was replaced by a quiet breathing mode with no detectable apnea episodes for the duration of the sleep cycle. A corollary effect of this disturbed sleep pattern, characterized by frequent daytime fatigue, and unavoidable early evening napping, was also observed to be eliminated while on the medication. This latter effect provides substantiating proof that the individual experienced a profound increase in the quality of night-time rest. The miotic agent used was the OCUSERT ® Pilo-20 (Alza Corp., Palo Alto, Calif. 94304) brand of pilocarpine in a composition with alginic acid surrounded by a hydrophobic ethylene/vinyl acetate copolymer membrane which produces a slow, sustained diffusion of pilocarpine into the localized membranes.

A recurrence of apnea/snoring episodes was observed to occur when the ocular patch neared its rated time of dissipation, or if a patch was inadvertently expelled prior to scheduled replacement. These observations have maintained a consistent pattern over an extended time period, with no apparent return of the apnea/snoring symptoms while on the medication. Other medications and/or dietary involvements have been discounted as contributing factors by a process of elimination and observation.

I claim:

1. A method for treating sleep apnea and hypopnea and snoring in a human patient suffering from such conditions which comprises administering ocularly to said patient a compound resulting in the release of pilocarpine to the surrounding tissue in an amount effective to reduce such apnea and hypopnea and/or snoring conditions in such patient.

2. A method according to claim 1 wherein the pilocarpine compound used to treat such patient is a pilocarpine salt.

3. A method according to claim 2 wherein the pilocarpine compound is pilocarpine hydrochloride.

4. A method according the claim 2 wherein the pilocarpine compound is pilocarpine nitrate.

5. A method according to claim 3 wherein the amount of pilocarpine hydrochloride administered to said patient is about 20 to 40 micrograms per hour.

6. A method according to claim 4 wherein the amount of pilocarpine nitrate is administered to said patient is about 20 to 40 micrograms per hour.

7. A method according to claim 5 wherein the pilocarpine hydrochloride is administered in a shaped dosage unit for continuous release over about one week per administration.

8. A method according to claim 6 wherein the pilocarpine nitrate is administered in a shaped dosage unit for continuous release over about one week per administration.

9. A method according to claim 1 wherein the pilocarpine compound is administered to said patient in the form of a shaped dosage placed in the cul-de-sac of the eye for continuous release of the pilocarpine compound over about one week per administration.

10. A method according to claim 9 wherein the pilocarpine compound administered to said patient is pilocarpine hydrochloride.

11. A method according to claim 9 wherein the pilocarpine compound administered to said patient is pilocarpine nitrate.

* * * * *